United States Patent [19]

Bremer et al.

[11] Patent Number: 5,643,874
[45] Date of Patent: Jul. 1, 1997

[54] PHARMACEUTICAL COMPOSITION COMPRISING A GLUCOSIDASE AND/OR AMYLASE INHIBITOR, AND A LIPASE INHIBITOR

[75] Inventors: Klaus-Dieter Bremer, Allschwil; Pavel Sawlewicz, Basel, both of Switzerland

[73] Assignee: Hoffmann-La Roche Inc., Nutley, N.J.

[21] Appl. No.: 279,127

[22] Filed: Jul. 22, 1994

[30] Foreign Application Priority Data

Aug. 5, 1993 [CH] Switzerland .................. 2339/93

[51] Int. Cl.$^6$ .................................................. A61K 38/00
[52] U.S. Cl. ........................... 514/12; 514/13; 514/54; 514/909
[58] Field of Search ........................ 514/12, 13, 54, 514/909

[56] References Cited

U.S. PATENT DOCUMENTS

| | | | |
|---|---|---|---|
| 4,189,438 | 2/1980 | Umezawa et al. | 260/343.9 |
| 4,254,256 | 3/1981 | Otani et al. | 536/18 |
| 4,273,765 | 6/1981 | Suhara et al. | 514/54 |
| 4,358,602 | 11/1982 | Umezawa et al. | 549/328 |
| 4,598,089 | 7/1986 | Hadvary et al. | 514/449 |
| 4,623,714 | 11/1986 | Vertesey et al. | 530/324 |
| 4,952,567 | 8/1990 | DeMeyts et al. | 514/54 |
| 5,036,081 | 7/1991 | Matsuo et al. | 514/336 |
| 5,240,962 | 8/1993 | Naktsu et al. | 514/570 |

FOREIGN PATENT DOCUMENTS

| | | |
|---|---|---|
| 0129748 | 6/1984 | European Pat. Off. . |
| 0364696 | 4/1990 | European Pat. Off. . |
| 89/11295 | 11/1989 | WIPO . |
| 92/05788 | 4/1992 | WIPO . |
| 93/07872 | 4/1993 | WIPO . |

OTHER PUBLICATIONS

Lehninger, Biochemistry, Second Edition, Worth Publishers, Inc., New York: 1975, p. 265.
Antidiabetic Agents, 30th Edition, Martindale Extra Pharmacopoeia, 276, no date available.
Hauptman et al., Initial Studies in Humans with the Novel Gastrointestinal Lipase Inhibitor Ro 18–0646 (tetrahydro–lipstatin)$^{1,2}$, Am. J. Nutr. 1992:55:309S–313S.
M. Negwer, Organic–Chemical Drugs and Their Synonyms, 6. Auflage, vol. II 1987, pp. 1310; 1311; 1547; 1652.
B.W. Bycroft, Dictionary of Antibiotics and Related Substances, 1988, Champman and Hall, London, New York, pp. 15; 298; 315; 445; 698.
Annual Drug Data Report (Published by Prous, Barcelona, Spain) (1992) 14(1), 46.
Annual Drug Data Report (Published by Prous, Barcelona, Spain) (1987) 9(7), 603.
Annual Drug Data Report (Published by Prous, Barcelona, Spain) (1986) 8(3), 276.
Annual Drug Data Report (Published by Prous, Barcelona, Spain) (1986) 8(?), 558.
Annual Drug Data Report (Published by Prous, Barcelona, Spain) (1990) 12(8), 636.
Annual Drug Data Report (Published by Prous, Barcelona, Spain) (1992) 14(7) 610.
Annual Drug Data Report (Published by Prous, Barcelona, Spain) (1992) 14(7), 606.
Federation Proceedings (1982) 41(3), 698.
WHO Chronicle (1980) 34 (Suppl.).
Int. J. Obesity, 1992; 16 (Suppl. 1):16, Abstr. 063.
Merck Index, 11th Ed. 1989 p. 4.
Annual Drug Data Report Dept. 1991, pp. 590–591.
Annual Drug Data Report p. 723 (1992).
Annual Drug Data Report p. 167 (1985).
Annual Drug Report p. 343 (1987).
J. Antibiotics XXXI No. 8, Kondo, et al., 1978.
J. of Antibiotics vol. 35, No. 9 (1982) pp. 1160–1166.
J. Antibiot. XL (1987) pp. 1647–1650.

*Primary Examiner*—Gary L. Kunz
*Attorney, Agent, or Firm*—George W. Johnston; Ellen Ciambrone Coletti

[57] ABSTRACT

A pharmaceutical composition containing a glucosidase and/or amylase inhibitor and a lipase inhibitor as active substances and usual pharmaceutical carriers.

21 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 74 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Streptomyces tendae ( i x ) FEATURE:
        ( A ) NAME/KEY: Disulfide-bond
        ( B ) LOCATION: 11..27

( i x ) FEATURE:
        ( A ) NAME/KEY: Disulfide-bond
        ( B ) LOCATION: 45..73

( x i ) SEQUENCE DESCRIPTION: SEQ ID NO:1:

```
Asp Thr Thr Val Ser Glu Pro Ala Pro Ser Cys Val Thr Leu Tyr Gln
 1               5                  10                 15

Ser Trp Arg Tyr Ser Gln Ala Asp Asn Gly Cys Ala Glu Thr Val Thr
            20                  25                 30

Val Lys Val Val Tyr Glu Asp Asp Thr Glu Gly Leu Cys Tyr Ala Val
        35                  40                 45

Ala Pro Gly Gln Ile Thr Thr Val Gly Asp Gly Tyr Ile Gly Ser His
    50                  55                 60

Gly His Ala Arg Tyr Leu Ala Arg Cys Leu
65                  70
```

( 2 ) INFORMATION FOR SEQ ID NO:2:

( i ) SEQUENCE CHARACTERISTICS:
        ( A ) LENGTH: 36 amino acids
        ( B ) TYPE: amino acid
        ( C ) STRANDEDNESS: double
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Streptomyces aureofaciens
        ( B ) STRAIN: FH1656

( i x ) FEATURE:
        ( A ) NAME/KEY: Cross-links
        ( B ) LOCATION: 8..25

( i x ) FEATURE:
        ( A ) NAME/KEY: Cross-links
        ( B ) LOCATION: 9..26

( i x ) FEATURE:

-continued

```
    ( A ) NAME/KEY: Peptide
    ( B ) LOCATION: 1..19

( i x ) FEATURE:
    ( A ) NAME/KEY: Peptide
    ( B ) LOCATION: 20..36

( i x ) FEATURE:
    ( A ) NAME/KEY: Cross-links
    ( B ) LOCATION: 20..36

( x i ) SEQUENCE DESCRIPTION: SEQ ID NO:2:

Ala Thr Gly Ser Pro Ala Pro Asp Ser Asp Ala Val Thr Val Val Val
 1               5                  10                  15

Gln Tyr Glu Gln Phe Ser Glu Val Cys Cys Gly Asn Arg Val Asp Thr
             20                  25                  30

Tyr Arg Trp Ser
         35
```

PHARMACEUTICAL COMPOSITION COMPRISING A GLUCOSIDASE AND/OR AMYLASE INHIBITOR, AND A LIPASE INHIBITOR

BRIEF SUMMARY OF THE INVENTION

The invention relates to pharmaceutical compositions containing an effective amount of at least one but no more than two glucosidase and/or amylase inhibitors and a lipase inhibitor as active substances; and the usual pharmaceutical carriers.

In another aspect, the invention relates to the use of at least one but no more than two glucosidase and/or amylase inhibitors for the combined simultaneous, separate or chronologically spaced use with a lipase inhibitor in the treatment of obesity.

DETAILED DESCRIPTION OF THE INVENTION

It has been found that such preparations can be used for the treatment of obesity.

Accordingly, the invention is also concerned with the use of at least one but no more than two glucosidase and/or amylase inhibitors for the combined simultaneous, separate or chronologically spaced use with a lipase inhibitor in the treatment of obesity.

Further, the invention is concerned with the use of at least one but no more than two glucosidase and/or amylase inhibitors in the manufacture of pharmaceutical compositions for the combined use with a lipase inhibitor in the treatment of obesity.

Examples of known glucosidase and/or amylase inhibitors which can be used, in accordance with the invention are:

O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4)O-α-D-glucopyranosyl-(1→4)-D-glucose, also known as acarbose;

2(S),3(R) ,4(S),5(S)-tetrahydroxy-N-[2-hydroxy-1-(hydroxymethyl)-ethyl]-5-(hydroxymethyl)-1(S)-cyclohexamine, also known as voglibose;

1,5-dideoxy-1,5-[(2-hydroxyethyl)imino]-D-glucitol, also known as miglitol;

1,5-dideoxy-1,5-[2-(4-ethoxycarbonylphenoxy)ethylimino]-D-glucitol, also known as emiglitate;

2,6-dideoxy-2,6-imino-7-(β-D-glucopyranosyl)-D-glycero-L-guloheptitol, also known as MDL-25637;

1,5-dideoxy-1,5-(6-deoxy-1-O-methyl-α-D-glucopyranos-6-ylimino)-D-glucitol, also known as camiglibose;

1,5,9,11,14-pentahydroxy-3-methyl-8,13-dioxo-5,6,8,13-tetrahydrobenzo[a]naphthacene-2-carboxylic acid, also known pradimicin Q;

```
                                10                                        20
Asp —Thr —Thr —Val —Ser —Glu —Pro —Ala —Pro —Ser —Cys —Val —Thr —Leu —Tyr —Gln —Ser —Trp —Arg —Tyr—
                                                    |
                                       30                                 40
Ser —Gln —Ala —Asp —Asn —Gly —Cys —Ala —Glu —Thr —Val —Thr —Val —Lys —Val —Val —Tyr —Glu —Asp —Asp—
                                       50                                 60
Thr —Glu —Gly —Leu —Cys —Tyr —Ala —Val —Ala —Pro —Gly —Gln —Ile —Thr —Thr —Val —Gly —Asp —Gly —Tyr—
                                       70
Ile —Gly —Ser —His —Gly —His —Ala —Arg —Tyr —Leu —Ala —Arg —Cys —Leu, also known as tendamistat [Seq ID : 1];
```

```
Pro —Ala —Pro —Asp —Ser —Asp —Ala —Val —Thr —Val —Val
 |         |    |                                   |
Ser       Val —Cys —Cys —Gly —Asn —Arg            Val
 |         |                       |               |
Gly       Glu                     Val             Gln
 |         |                       |               |
Thr       Ser                     Asp             Tyr
 |         |                       |               |
Ala       Phe                     Thr             Glu
           |                       |
          Gln — Ser — Trp — Arg — Tyr, also known as AI-3688 [SEQ ID: 2];
```

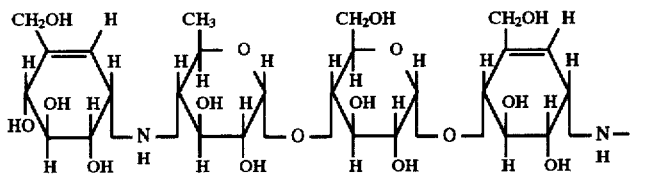

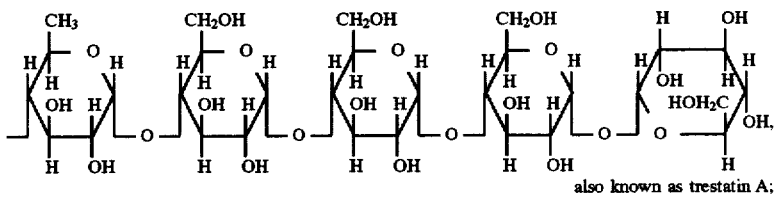

also known as trestatin A;

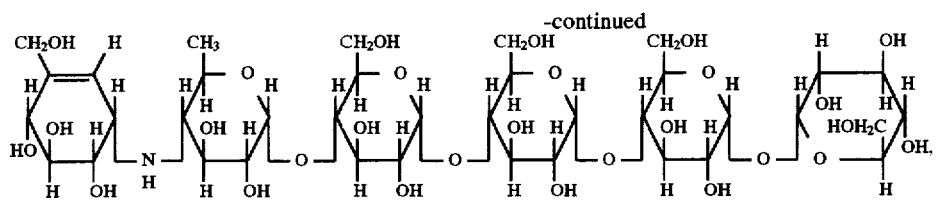

also known as trestatin B;

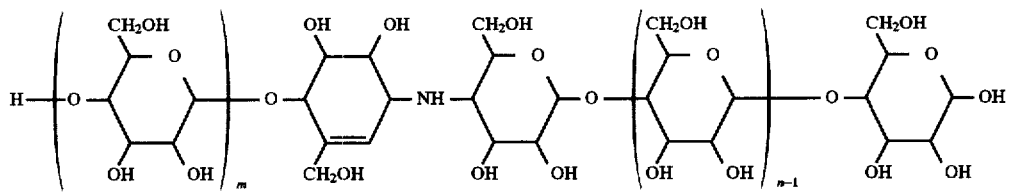

wherein m is an integer of 0 to 8, n is an integer of 1 to 8 and m+n is an integer of 1 to 8, also known as adiposine; and 1,2-dideoxy-2-[2(S),3(S),4(R)-trihydroxy-5-(hydroxymethyl)-5-cyclohexen-1(S)-ylamino]-L-glucopyranose, also known as salbostatin.

Examples of known lipase inhibitors are:

(2S,3S,5S)-5-[(S)-2-formamido-4-methyl-valeryloxy]-2-hexyl-3-hydroxy-hexadecanoic 1,3 acid lactone, also known as tetrahydrolipstatin (previously also known as Orlistat);

(2S,3S,5S,7Z,10Z)-5-[(S)-2-formamido-4-methyl-valeryloxy]-2-hexyl-3-hydroxy-7,10-hexadecadienoic 1,3 acid lactone, also known as lipstatin;

1-(trans-4-isobutylcyclohexyl)-2-(phenylsulfonyloxy) ethanone, also known as FL-386;

4-methylpiperidine-1-carboxylic acid 4-phenoxyphenyl ester, also known as WAY-121898;

N-[3-chloro-4-(trifluoromethyl)phenyl-]N'-[3-(trifluoromethyl)-phenyl]urea, also known as BAY-N-3176;

N-formyl-L-valine-(S)-1-[[(2S, 3S)-3-hexyl-4-oxo-2-oxetanyl]methyl]hexyl ester, also known as valilactone;

(2S,3S,5S,7Z,10Z)-5-[(S)-2-acetamido-3-carbamoylpropionyloxy]-2-hexyl-3-hydroxy-7,10-hexadecadienoic lactone, also known as esterastin;

(3S,4S)-4-[(1S,5R,7S,8R,9R,E)-8-hydroxy 1,3,5,7,9-pentamethyl-6-oxo-3-undecenyl]-3-methyl-2-oxetanone, also known as ebelactone A;

(3S,4S)-3-ethyl-4-[(1S,5R,7S,8R,9R,E)-8-hydroxy-1,3,5,7,9-pentamethyl-6-oxo-3-undecenyl]-2-oxetanone, also known as ebelactone B; and 1,6-di(O-(carbamoyl)cyclohexanone oxime)hexane, also known as RHC 80267.

Biomasses or fermentation cakes which result in the fermentative manufacture of lipase inhibitors, such as, (2S,3S,5S, 7Z,10Z)-5-[(S)-2-formamido-4-methyl-valeryloxy]-2-hexyl-3-hydroxy-7,10-hexadecadienoic 1,3 acid lactone also known as lipstatin or (2S,3S,5S,7Z,10Z)-5-[(S)-2-acetamido-3-carbamoyl-propionyloxy]-2-hexyl-3-hydroxy-7,10-hexadecadienoic lactone also known as esterastin, can also be used as the lipase inhibitor. The latter are described, for example, in EP-A 129 748 and U.S. Pat. No. 4,189,438.

It is known that either glucosidase inhibitors or amylase inhibitors or both, such as, O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4)O-α-D-glucopyranosyl-(1→4)-D-glucose also known as acarbose, retard the digestion of carbohydrates.

It is also known that lipase inhibitors, such as, (2S,3S,5S)-5-[(S)-2-formamido-4-methyl-valeryloxy]-2-hexyl-3-hydroxy-hexadecanoic 1,3 acid lactone also known as tetrahydrolipstatin, give rise to a partial inhibition of lipase in the intestine.

However, in monotherapy lipase inhibitors themselves in combination with a reduction diet generally bring about only a moderate weight loss and glucosidase and/or amylase inhibitors bring about practically no weight loss. It has now been surprisingly found that a combined use of a glucosidase and/or amylase inhibitor and a lipase inhibitor leads to a substantially greater weight loss than in the case of monotherapy. This has been demonstrated in the following test:

The test was carried out in two trial periods on two volunteers (A and B). The average daily calorie amounts of 2560 Kcal for A and 1850 Kcal for B were determined in a 7 day preliminary trial in which the volunteers took no medication. The volunteers were given 120 mg of (2S,3S,5S)-5-[(S)-2-formamido 4-methyl-is valeryloxy]-2-hexyl-3-hydroxy-hexadecanoic 1,3 acid lactone also known as tetrahydrolipstatin and 100 mg of O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4) O-α-D-glucopyranosyl-(1→4)-D-glucose also known as acarbose at each meal time in the subsequent 14 day main trial. A special diet was not adhered to and physical activities were reduced to a minimum. Here, as in the preliminary trial, the average daily calorie amounts of 2185 Kcal for A and 2050 Kcal for B were also ascertained. The weight loss of both volunteers will be evident from the following Table.

|  | Body weight | |
| --- | --- | --- |
| Trial day | A | B |
| 1 | 74.3 | 88.7 |
| 2 | 74.1 | 88.5 |
| 3 | 74.6 | 89.1 |
| 4 | 73.9 | 88.0 |
| 5 | 73.5 | 88.4 |
| 6 | 73.3 | 88.2 |
| 7 | 73.0 | 87.7 |
| 8 | 73.6 | 87.8 |
| 9 | 73.3 | 87.7 |
| 10 | 73.1 | 87.4 |
| 11 | 72.8 | 87.2 |
| 12 | 72.4 | 87.5 |
| 13 | 72.4 | 87.2 |
| 14 | 72.2 | 86.4 |
| 15 | 71.9 | 86.1 |
| Weight loss | 2.4 | 2.6 |

In comparison to the above result, the weight loss of patients in the case of monotherapy with tetrahydrolipstatin (3×120 mg/day) in a placebo-controlled 12 weeks trial was on average 1.8 kg (i.e. 0.3 kg/14 days) (Int. J. Obesity 1992; 16 (Suppl. 1): 16, Abstr. 063).

In accordance with the invention, at least one but no more than two inhibitors of the glucosidase and/or amylase can be used in the form of pharmaceutical compositions in combination with a lipase inhibitor for the simultaneous, separate or chronologically spaced use in the treatment of obesity.

The use of O-4,6-dideoxy-4-[[[1S-(1α,4α,5β,6α, )]-4,5, 6-trihydroxy-3-(hydroxymethyl)-2-cyclohexen-1-yl]amino] -α-D-glucopyranosyl-(1→4)O-α-D-glucopyranosyl-(1→4) -D-glucose also known as acarbose and (2S,3S,5S)-5-[(S)- 2-formamido-4-methyl-valeryloxy]-2-hexyl-3-hydroxy- hexadecanoic 1,3 acid lactone also known as tetrahydrolipstatin is preferred.

The active ingredients are administered orally for the treatment of obesity.

They can be administered daily in dosages of about 0.003 mg to about 20 mg, preferably 0.015 mg to 10 mg, of glucosidase and/or amylase inhibitor and of about 0.15 mg to 20 mg, preferably 0.5 mg to 10 mg, of lipase inhibitor per kg body weight.

The compositions, in accordance with the invention, can be incorporated into standard pharmaceutical dosage forms, for example, they are useful for oral application with the usual pharmaceutical adjuvant material, for example, organic or inorganic inert carrier materials, such as, water, gelatin, lactose, starch, magnesium stearate, talc, gums, polyalkyleneglycols and the like. The pharmaceutical preparations can be employed in a solid form, for example, as tablets, capsules, or in liquid form, for example, as solutions, or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

Solid dosage forms such as tablets and capsules conveniently contain per dosage unit about 0.2 mg to about 100 mg of glucosidase and/or amylase inhibitor and 10 mg to 200 mg of lipase inhibitor.

In addition to the treatment of obesity, the compositions or active substance combination, in accordance with the invention, can be used for the treatment and prevention of illnesses which frequently occur in association with overweight, such as diabetes, hypertension, hyperlipidemia and insulin-resistance syndrome.

In the case of all of these indications, the active substances can be used in the dosage ranges given above, with the individual dosage depending on the nature of the illness to be treated as well as on the age and condition of the patient and can be determined within the purview of the medical specialist.

The invention is illustrated in more detail by the following Examples.

Pharmaceutical compositions of the following composition are produced in a known manner:

EXAMPLE A

| Soft gelatin capsules | |
| --- | --- |
| | Amount per capsule |
| Tetrahydrolipstatin | 60 mg |
| Medium chain triglyceride | 450 µl |
| Acarbose | 50 mg |

EXAMPLE B

| Hard gelatin capsules | |
| --- | --- |
| Acarbose | 25.0 mg |
| Tetrahydrolipstatin | 30.0 mg |
| Cryst. lactose | 37.0 mg |
| Microcrystalline cellulose | 20.0 mg |
| Polyvinylpolypyrrolidone | 8.5 mg |
| Sodium carboxymethylstarch | 8.5 mg |
| Talc | 4.5 mg |
| Magnesium stearate | 1.5 mg |
| Capsule fill weight | 135.0 mg |

| Tablets | |
| --- | --- |
| Acarbose | 25.0 mg |
| Tetrahydrolipstatin | 30.0 mg |
| Anhydrous lactose | 118.8 |
| Microcrystalline cellulose | 30.0 |
| Polyvinylpolypyrrolidone | 10.0 |
| Carboxymethylcellulose | 10.0 |
| Magnesium stearate | 1.2 |
| Tablet weight | 225.0 mg |

EXAMPLE D

| Tablets having controlled active substance release and increased residence time in the stomach | |
| --- | --- |
| Acarbose | 50.0 mg |
| Tetrahydrolipstatin | 60.0 mg |
| Powd. lactose | 70.0 mg |
| Hydroxypropylmethylcellulose | 52.5 mg |
| Polyvinylpolypyrrolidone | 7.5 mg |
| Talc | 8.0 mg |
| Magnesium stearate | 1.0 mg |
| Colloidal silicic acid | 1.0 mg |
| Core weight | 250.0 mg |
| Hydroxypropylmethylcellulose | 2.5 mg |
| Talc | 1.25 mg |
| Titanium dioxide | 1.25 mg |
| Film coating weight | 5.0 mg |

EXAMPLE E

| Powder for reconstitution | |
| --- | --- |
| Acarbose | 100.0 mg |
| Tetrahydrolipstatin | 120.0 mg |
| Ethylvanillin | 10.0 mg |
| Aspartame | 30.0 mg |
| Sprayed skimmed milk powder | 4740.0 mg |
| Total | 5000.0 mg |

The formulation of Examples A–E can be prepared by known methods.

We claim:

1. A pharmaceutical composition which comprises an effective amount of a lipase inhibitor and (a) a glucosidase inhibitor, (b) an amylase inhibitor or, (c) a glucosidase and amylase inhibitor, together with an inert carrier.

2. A pharmaceutical composition according to claim 1, wherein the daily dosage of a lipase inhibitor is 0.15 to 20 mg per Kg body weight and the daily dosage of said glucosidase inhibitor, amylase inhibitor or glucosidase and amylase inhibitor is 0.003 to 20 mg per Kg body weight.

3. A pharmaceutical composition according to claim 1, in the form of a solid dosage unit comprising per dosage unit 10 to 200 mg of a lipase inhibitor and 0.2 to 100 mg of said glucosidase inhibitor, amylase inhibitor or glucosidase and amylase inhibitor.

4. A pharmaceutical composition according to claim 2, wherein the lipase inhibitor is selected from the group consisting of (2S,3S,5S)-5-[(S)-2-formamido-4-methyl-valeryloxy]-2-hexyl-3-hydroxy-hexadecanoic 1,3 acid lactone, (2S,3S,5S,7Z,10Z)-5-[(S)-2-formamido-4-methyl-valeryloxy]-2-hexyl-3-hydroxy-7,10-hexadecadienoic 1,3 acid lactone, 1-(trans-4-isobutylcyclohexyl)-2-(phenylsulfonyloxy) ethanone, 4-methylpiperidine-1-carboxylic acid 4-phenoxyphenyl ester, N-[3-chloro-4-(trifluoromethyl)phenyl-N'-[3-(trifluoromethyl)phenyl]urea; N-formyl-L-valine-(S)-1-[[(2S,3S)-3-hexyl-4-oxo-2-oxetanyl]methyl]hexyl ester, (2S,3S, 5S,7Z,10Z)-5-[(S)-2-acetamido-3-carbamoylpropionyloxy]-2-hexyl-3-hydroxy-7,10-hexadecadienoic lactone, (3S,4S)-4-[(1S,5R,7S,8R, 9R,E)-8-hydroxy-1,3,5,7,9-pentamethyl-6-oxo-3-undecenyl]-3-methyl-2-oxetanone, (3S,4S)-3-ethyl-4-[(1S, 5R, 7S,8R,9R,E)-8-hydroxy-1,3,5,7,9-pentamethyl-6-oxo-3-undecenyl]-2-oxetanone, and 1,6-di(O-(carbamoyl)cyclohexanone oxime)hexane.

5. A pharmaceutical composition according to claim 2, wherein the lipase inhibitor is (2S,3S,5S)-5-[(S)-2-formamido-4-methyl-valeryloxy]-2-hexyl-3-hydroxy-hexadecanoic 1,3 acid lactone.

6. A method for treating obesity which comprises administering to a host in need of such treatment an effective amount of a lipase inhibitor and (a) glucosidase inhibitor, (b) amylase inhibitor, (c) or a glucosidase and amylase inhibitor.

7. A method for treating obesity which comprises administering a lipase inhibitor and (a) a glucosidase inhibitor, (b) amylase inhibitor, or (c) a glucosidase and amylase inhibitor in a simultaneous, separate, or chronologically spaced manner.

8. A method according to claim 6, wherein the daily dosage of lipase inhibitor is 0.15 to 20 mg per Kg body weight and the daily dosage of said glucosidase inhibitor, amylase inhibitor or glucosidase and amylase inhibitor is 0.003 to 20 mg per Kg body weight.

9. A method according to claim 6, wherein the lipase inhibitor and (a) glucosidase inhibitor, (b) amylase inhibitor, or (c) glucosidase and amylase inhibitor are administered in a solid dosage unit comprising per dosage unit 10 to 200 mg of lipase inhibitor and 0.2 to 100 mg of the (a) glucosidase inhibitor, (b) amylase inhibitor, or (c) glucosidase and amylase inhibitor.

10. A method according to claim 7, wherein the lipase is inhibitor is selected from the group consisting of (2S,3S, 5S)-5-[(S)-2-formamido-4-methyl-valeryloxy]-2-hexyl-3-hydroxy-hexadecanoic 1,3 acid lactone, (2S,3S,5S, 7Z,10Z)-5-[(S)-2-formamido-4-methyl-valeryloxy]-2-hexyl-3-hydroxy-7,10-hexadecadienoic 1,3 acid lactone, 1-(trans-4-isobutylcyclohexyl)-2-(phenyl-sulfonyloxy)ethanone, 4-methyl-piperidine-1-carboxylic acid 4-phenoxyphenyl ester, N-[3-chloro-4-(trifluoromethyl)phenyl-N'-[3-(trifluoromethyl)phenyl]urea, N-formyl-L-valine-(S)-1-[[(2S,3S)-3-hexyl-4-oxo-2-oxetanyl]methyl]hexyl ester, (2S ,3S,5S ,7Z, 10Z)-5-[(S)-2-acetamido-3-carbamoyl-propionyloxy]-2-hexyl-3-hydroxy-7,10-hexadecadienoic lactone, (3S,4S)-4-[(1S,5R,7S,8R,9R,E)-8-hydroxy-1,3,5,7, 9-pentamethyl-6-oxo-3-undecenyl]-3-methyl-2-oxetanone, (3S,4S)-3-ethyl-4-[(1S,5R,7S, 8R,9R,E)-8-hydroxy-1,3,5,7, 9-pentamethyl-6-oxo-3-undecenyl]-2-oxetanone, and 1,6-di (O-(carbamoyl)cyclohexanone oxime)hexane.

11. A pharmaceutical composition according to claim 2, wherein the (a) glucosidase inhibitor, (b) amylase inhibitor or (c) glucosidase and amylase inhibitor is selected from the group consisting of O-4,6-Dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4) O-α-D-glucopyranosyl-(1→4)-D-glucose, 2(S),3(R),4(S),5(S)-tetrahydroxy-N-[2-hydroxy-1-(hydroxymethyl)-ethyl]-5-(hydroxymethyl)-1(S)-cyclohexamine, 1,5-dideoxy-1,5-[(2-hydroxyethyl)imino]-D-glucitol,1,5-dideoxy-1,5-[2-(4-ethoxy-carbonylphenoxy)ethylimino]-D-glucitol, 2,6-dideoxy-2,6-imino-7-(β-D-glucopyranosyl)-D-glycero-L-gulo-heptitol, 1,5-dideoxy-1,5-(6-deoxy-1-O-methyl-α-D-glucopyranos-6-ylimino)-D-glucitol,

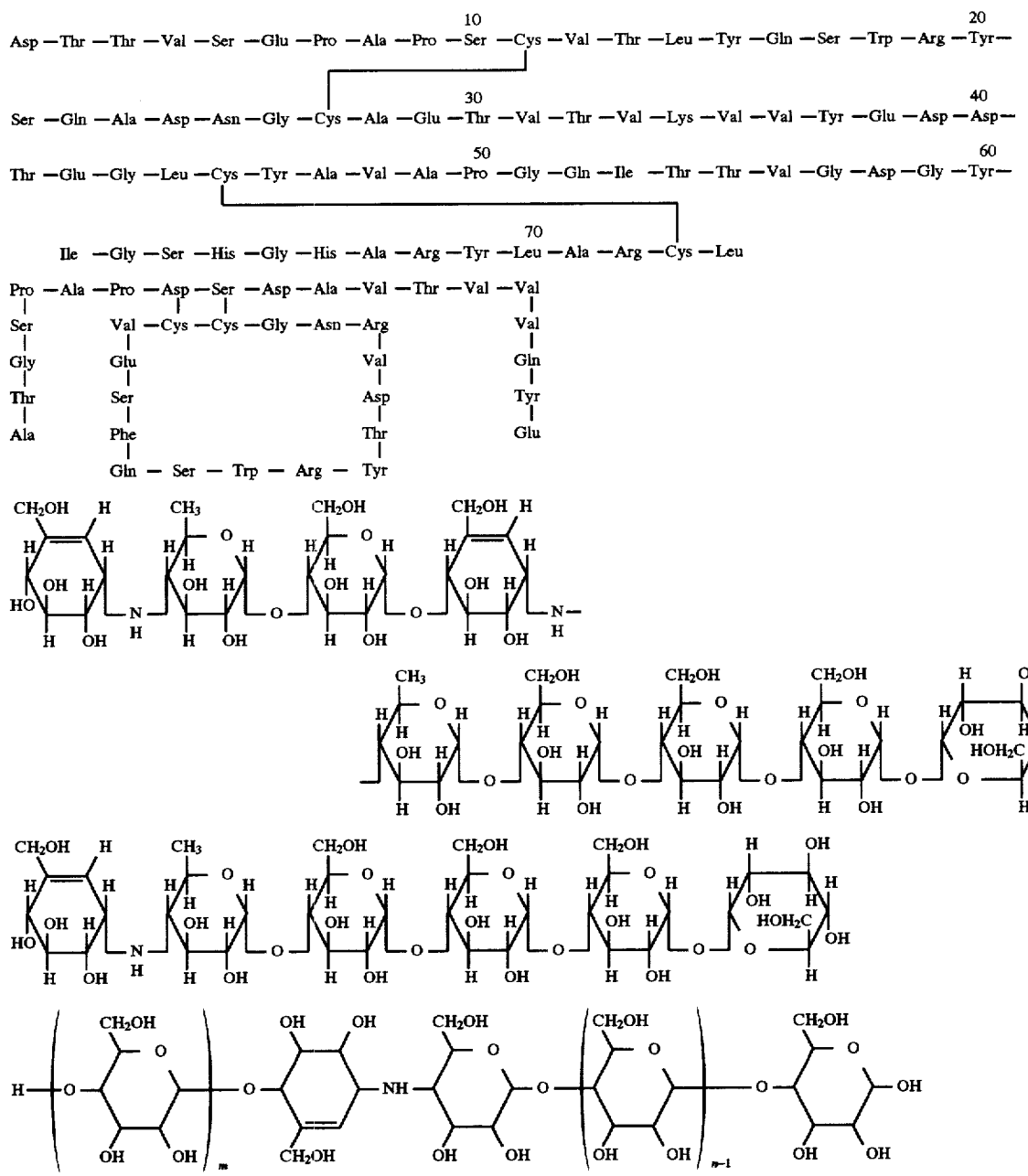

wherein m is an integer of 0 to 8, n is an integer of 1 to 8 and m+n is an integer of 1 to 8,
1,5,9,11,14-pentahydroxy-3-methyl-8,13-dioxo-5,6,8,13-tetrahydrobenzo[a]naphthacene-2-carboxylic acid, and 1,2-dideoxy-2-[2(S),3(S),4(R)-trihydroxy-5-(hydroxymethyl)-5-cyclohexen-1(S)-ylamino]-L-glucopyranose.

12. A pharmaceutical composition according to claim 2, wherein the (a) glucosidase inhibitor, (b) amylase inhibitor, or (c) glucosidase and amylase inhibitor is O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4) O-α-D-glucopyranosyl-(1→4)-D-glucose.

13. A method according to claim 7, wherein the (a) glucosidase inhibitor, (b) amylase inhibitor, or (c) glucosidase and amylase inhibitor is selected from the group consisting of O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4) O-α-D-glucopyranosyl-(1→4)-D-glucose, 2(S),3(R),4(S),5(S)-tetrahydroxy-N-[2-hydroxy-1-(hydroxymethyl)ethyl]-5-(hydroxymethyl)-1(S)-cyclohexamine, 1,5-dideoxy-1,5-[(2-hydroxyethyl)imino]-D-glucitol,1,5-dideoxy-,1,5-[2-(4-ethoxy-carbonylphenoxy) ethylimino]-D-glucitol, 2,6-dideoxy-2,6-imino-7-(β-D-glucopyranosyl)-D-glycero-L-gulo-heptitol, 1,5-dideoxy-,1, 5-(6-deoxy-1-O-methyl-α-D-glucopyranos-6-ylimino)-D-glucitol.

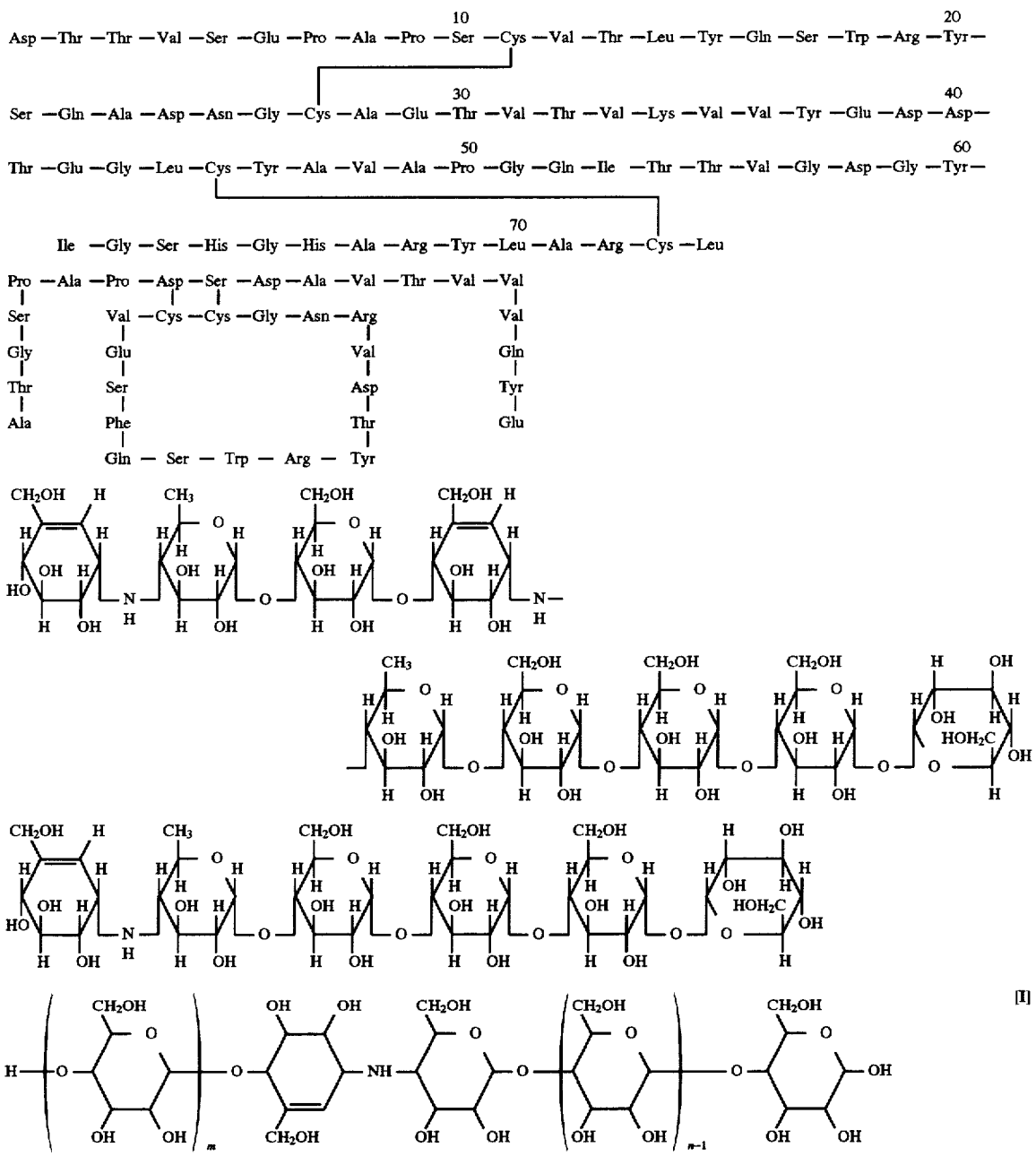

wherein m is an integer of 0 to 8, n is an integer of 1 to 8 and m+n is an integer of 1 to 8, 1,5,9,11,14-pentahydroxy-3-methyl-8,13-dioxo-5,6,8,13-tetrahydrobenzo[a]naphthacene-2-carboxylic acid, and 1,2-dideoxy-2-[2(S),3(S),4(R)-trihydroxy-5-(hydroxymethyl)-5-cyclohexen-1(S)-ylamino]-L-glucopyranose.

14. A method according to claim 7, wherein the (a) glucosidase inhibitor, (b) amylase inhibitor, or (c) glucosidase and amylase inhibitor is O-4,6-dideoxy-4-[[[1S-(1α, 4α,5β,6α)]-4,5,6-trihydroxy-3-(hydroxymethyl)-2-cyclohexen-1-yl]amino]-α-D-glucopyranosyl-(1→4) O-α-D-glucopyranosyl-(1→4)-D-glucose.

15. A pharmaceutical composition which comprises an effective amount of (2S,3S,5S)-5-[(S)-2-formamido-4-methyl-valeryloxy]-2-hexyl-3-hydroxy-hexadecanoic 1,3 and lactone; O-4,6-dideoxy -4-[[[1S-(1α4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose and an inert carrier.

16. A pharmaceutical composition according to claim 15, wherein the daily dosage of (2S,3S,5S)-5-[(S)-2-formamido-4-methyl-valeryloxy]-2-hexyl-3-hydroxy-hexadecanoic 1,3 acid lactone is 0.15 to 20 mg per kg body weight and the daily dosage of O-4,6-dideoxy-4-[[[1S-(1α, 4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose is 0.003 to 20 mg per kg body weight.

17. A pharmaceutical composition according to claim 15, in the form of a solid dosage unit comprising per dosage unit 10 to 200 mg of (2S,3 S,5S)-5-[(S)-2-formamido-4-methyl-valeryloxy]-2-hexyl-3-hydroxy-hexadecanoic 1,3 acid lactone and 0.2 to 100 mg of O-4,6-dideoxy- 4-[[[1S-(1α,4α, 5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose.

18. A method for treating obesity which comprises administering to a host in need of such treatment an effective amount of (2S,3S,5S)-5-[(S)-2-formamido-4-methyl-valeryloxy]-2-hexyl-3-hydroxy-hexadecanoic 1,3 acid lactone and O-4,6-dideoxy-4-[[[1S-(1α,4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose.

19. A method for treating obesity which comprises administering to a host in need of such treatment (2S,3S,5S)-5-[(S)-2-formamido-4-methyl-valeryloxy]-2-hexyl-3-hydroxy-hexadecanoic 1,3 acid lactone and O-4,6-dideoxy-4-[[[1S-(1α,4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose in a simultaneous, separate, or chronologically spaced manner.

20. A method according to claim 18, wherein the daily dosage of (2S,3S,5S)-5-[(S)-2-formamido-4-methyl-valeryloxy]-2-hexyl-3-hydroxy-hexadecanoic 1,3 acid lactone is 0.15 to 20 mg per kg body weight and the daily dosage of O-4,6-dideoxy-4-[[[1S-(1α,4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose is 0.003 to 20 mg per kg body weight.

21. A method according to claim 18, wherein (2S,3S,5S)-5-[(S)-2-formamido-4-methyl-valeryloxy]-2-hexyl-3-hydroxy-hexadecanoic 1,3 acid lactone and O-4,6-dideoxy-4-[[[1S-(1α,4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose are administered in a solid dosage unit comprising per dosage unit 10 to 200 mg of (2S,3S,5S)-5-[(S)-2-formamido-4-methyl-valeryloxy]-2-hexyl-3-hydroxy-hexadecanoic 1,3 acid lactone and 0.2 to 100 mg of O-4,6-dideoxy-4-[[[1S-(1α,4α,5β,6α)]-4,5,6-trihydroxy-3-(hydroxymethyl-2-cyclohexen-1-yl]amino]-α-D-glucopyranosyl-(1→4) O-α-D-glucopyranosyl-(1→4)-D-glucose.

* * * * *